(12) United States Patent
Demmitt

(10) Patent No.: US 9,069,358 B2
(45) Date of Patent: Jun. 30, 2015

(54) SYSTEM FOR CONTROLLING AND OPTIMIZING REACTIONS IN SOLID PHASE SYNTHESIS OF SMALL MOLECULES

(71) Applicant: Biolytic Lab Performance, Inc., Fremont, CA (US)

(72) Inventor: Thomas J. Demmitt, Fremont, CA (US)

(73) Assignee: Biolytic Lab Performance, Inc., Fremont, CA (US)

(*) Notice: Subject to any disclaimer, the term of this patent is extended or adjusted under 35 U.S.C. 154(b) by 172 days.

(21) Appl. No.: 13/925,642

(22) Filed: Jun. 24, 2013

(65) Prior Publication Data

US 2014/0377134 A1 Dec. 25, 2014

(51) Int. Cl.
*G01N 35/10* (2006.01)
*G05D 7/06* (2006.01)
*G05D 16/00* (2006.01)
*G01N 35/00* (2006.01)
*B01J 3/04* (2006.01)
*C07K 1/00* (2006.01)

(52) U.S. Cl.
CPC .............. *G05D 7/0605* (2013.01); *G05D 16/00* (2013.01); *G01N 35/00* (2013.01); *G01N 35/10* (2013.01); *B01J 3/042* (2013.01); *C07K 1/00* (2013.01)

(58) Field of Classification Search
CPC ...... G01N 35/10; G01N 35/00; G05D 7/0605; G05D 16/00
USPC ............. 422/64, 63, 131, 136, 134, 112, 114; 137/1
See application file for complete search history.

(56) References Cited

U.S. PATENT DOCUMENTS

| 2,434,167 | A | 1/1948 | Knoblauch |
| 2,684,255 | A | 7/1954 | Abele et al. |
| 3,215,500 | A | 11/1965 | Bittner |
| 3,538,950 | A | 11/1970 | Porteners |
| 3,583,230 | A | 6/1971 | Patterson |
| 3,645,142 | A | 2/1972 | Turpin |
| 3,838,013 | A | 9/1974 | Bergeron |
| 3,844,306 | A | 10/1974 | Hill |
| 3,917,455 | A | 11/1975 | Bak et al. |
| 4,114,853 | A | 9/1978 | Medvick |
| 4,353,989 | A | 10/1982 | Bender et al. |
| 4,360,360 | A | 11/1982 | Chiknas |
| 4,415,732 | A | 11/1983 | Caruthers et al. |

(Continued)

OTHER PUBLICATIONS

Printout: "ABI 3900 Synthsizer", Azco Biotech, Inc., http://www.azcobiotech.com/instruments/3900.php, Mar. 24, 2014.

(Continued)

*Primary Examiner* — Walter D Griffin
*Assistant Examiner* — Huy-Tram Nguyen
(74) *Attorney, Agent, or Firm* — Thomas Schneck

(57) ABSTRACT

A instrument for performing synthesis of small molecules such as Oligos and Peptides when using solid phase synthesis techniques to synthesize small molecules. The system and methods include a mechanism for controlling the pressure differential across the reaction vessels that contain the solid support used in solid phase synthesis. Reaction vessels are held in a holder that provides a sealable chamber at the outlet ends of the reaction vessels. The rotor containing the reaction vessels is placed within a sealable chamber. The sealable chamber is fitted with a means for engaging the rotor and draining the reaction vessels to waste. The sealable chamber is also fitted with a means for engaging the rotor to drain the reaction vessels at a slower, variable rate.

17 Claims, 15 Drawing Sheets

(56) References Cited

U.S. PATENT DOCUMENTS

| | | |
|---|---|---|
| 4,458,066 A | 7/1984 | Caruthers et al. |
| 1,748,859 A | 6/1988 | Magnussen, Jr. et al. |
| 4,810,471 A | 3/1989 | Wachob et al. |
| 4,816,513 A | 3/1989 | Bridgham et al. |
| 4,837,159 A | 6/1989 | Yamada |
| 4,849,648 A | 7/1989 | Longardner |
| 4,874,691 A | 10/1989 | Chandler |
| 4,882,127 A | 11/1989 | Rosenthal et al. |
| 5,047,524 A | 9/1991 | Andrus et al. |
| 5,048,578 A | 9/1991 | Dorf et al. |
| 5,053,454 A | 10/1991 | Judd |
| 5,066,600 A | 11/1991 | Antonevich et al. |
| 5,093,268 A | 3/1992 | Leventis et al. |
| 5,096,807 A | 3/1992 | Leaback |
| 5,112,736 A | 5/1992 | Caldwell et al. |
| 5,132,418 A | 7/1992 | Caruthers et al. |
| 5,147,608 A | 9/1992 | Hudson et al. |
| 5,171,537 A | 12/1992 | Wainwright et al. |
| 5,239,484 A | 8/1993 | Hayashi et al. |
| 5,240,680 A | 8/1993 | Zuckermann et al. |
| 5,252,296 A | 10/1993 | Zuckermann et al. |
| 5,262,530 A | 11/1993 | Andrus et al. |
| 5,273,718 A | 12/1993 | Skold et al. |
| 5,297,288 A | 3/1994 | Hemminger et al. |
| 5,324,483 A | 6/1994 | Cody et al. |
| 5,344,613 A | 9/1994 | Nokihara et al. |
| 5,356,776 A | 10/1994 | Kambara et al. |
| 5,368,823 A | 11/1994 | McGraw et al. |
| 5,380,495 A | 1/1995 | Chang et al. |
| 5,395,594 A | 3/1995 | Nokihara et al. |
| 5,405,585 A | 4/1995 | Coassin |
| 5,424,038 A | 6/1995 | Benz et al. |
| 5,427,930 A | 6/1995 | Birkenmeyer et al. |
| 5,437,979 A | 8/1995 | Rampal et al. |
| 5,453,247 A | 9/1995 | Beavis et al. |
| 5,468,606 A | 11/1995 | Bogart et al. |
| 5,472,672 A | 12/1995 | Brennan |
| 5,483,843 A | 1/1996 | Miller et al. |
| 5,496,523 A | 3/1996 | Gazit et al. |
| 5,503,805 A | 4/1996 | Sugarman et al. |
| 5,510,270 A | 4/1996 | Fodor et al. |
| 5,522,272 A | 6/1996 | Vecere et al. |
| 5,529,756 A | 6/1996 | Brennan |
| 5,541,113 A | 7/1996 | Siddigi et al. |
| 5,545,531 A | 8/1996 | Rava et al. |
| 5,547,839 A | 8/1996 | Dower et al. |
| 5,556,598 A | 9/1996 | Raybuck et al. |
| 5,563,033 A | 10/1996 | Lawrence et al. |
| 5,571,639 A | 11/1996 | Hubbell et al. |
| 5,575,914 A | 11/1996 | Jeyendran |
| 5,593,839 A | 1/1997 | Hubbell et al. |
| 5,597,694 A | 1/1997 | Munroe et al. |
| 5,605,662 A | 2/1997 | Heller et al. |
| 5,609,826 A | 3/1997 | Cargill et al. |
| 5,632,957 A | 5/1997 | Heller et al. |
| 5,633,365 A | 5/1997 | Stokke et al. |
| 5,639,428 A | 6/1997 | Cottingham |
| 5,645,114 A | 7/1997 | Bogen et al. |
| 5,645,801 A | 7/1997 | Bouma et al. |
| 5,648,266 A | 7/1997 | Astle |
| 5,653,939 A | 8/1997 | Hollis et al. |
| 5,690,894 A | 11/1997 | Pinkel et al. |
| 5,707,797 A | 1/1998 | Windle |
| 5,720,923 A | 2/1998 | Haff et al. |
| 5,720,928 A | 2/1998 | Schwartz |
| 5,736,333 A | 4/1998 | Livak et al. |
| 5,744,305 A | 4/1998 | Fodor et al. |
| 5,746,976 A | 5/1998 | Yamada et al. |
| 5,762,881 A | 6/1998 | Harness et al. |
| 5,770,157 A | 6/1998 | Cargill et al. |
| 5,807,523 A | 9/1998 | Watts et al. |
| 5,849,247 A | 12/1998 | Uzan et al. |
| 5,851,491 A | 12/1998 | Moulton |
| 5,855,852 A | 1/1999 | Bienhaus et al. |
| 5,861,094 A | 1/1999 | Goehde |
| 5,882,601 A | 3/1999 | Kath et al. |
| 5,976,470 A | 11/1999 | Maiefski et al. |
| 6,048,457 A | 4/2000 | Kopaciewicz et al. |
| 6,083,682 A | 7/2000 | Campbell et al. |
| 6,123,905 A | 9/2000 | Torti et al. |
| 6,126,904 A | 10/2000 | Zuellig et al. |
| 6,133,045 A | 10/2000 | Johnson et al. |
| 6,171,555 B1 | 1/2001 | Cargill et al. |
| RE37,194 E | 5/2001 | Kirk et al. |
| 6,264,891 B1 | 7/2001 | Heyneker et al. |
| 6,270,730 B1 | 8/2001 | McLuen et al. |
| 6,296,762 B1 | 10/2001 | Jonsson et al. |
| 6,416,718 B1 | 7/2002 | Maiefski et al. |
| 6,432,365 B1 | 8/2002 | Levin et al. |
| 6,537,504 B1 | 3/2003 | Young |
| 6,566,145 B2 | 5/2003 | Brewer |
| 6,673,317 B2 | 1/2004 | Hashimoto et al. |
| 6,720,143 B2 | 4/2004 | Juncosa et al. |
| 6,811,755 B2 | 11/2004 | McLuen et al. |
| 7,435,390 B2 * | 10/2008 | Cracauer et al. ............... 422/130 |
| 2001/0000723 A1 | 5/2001 | McLuen et al. |
| 2001/0001035 A1 | 5/2001 | McLuen et al. |
| 2001/0007644 A1 | 7/2001 | McLuen et al. |
| 2001/0026772 A1 | 10/2001 | Fuerst et al. |
| 2001/0051114 A1 | 12/2001 | McLuen et al. |
| 2001/0053335 A1 | 12/2001 | Hashimoto et al. |
| 2003/0211539 A1 | 11/2003 | Frank et al. |

OTHER PUBLICATIONS

Prinout: "DNA/RNA Synthesizers", ABI 3900 upgrade, Blue Lion Biotech, http://www.bluelionbio.com/labequip.phtml, Mar. 24, 2014.

* cited by examiner

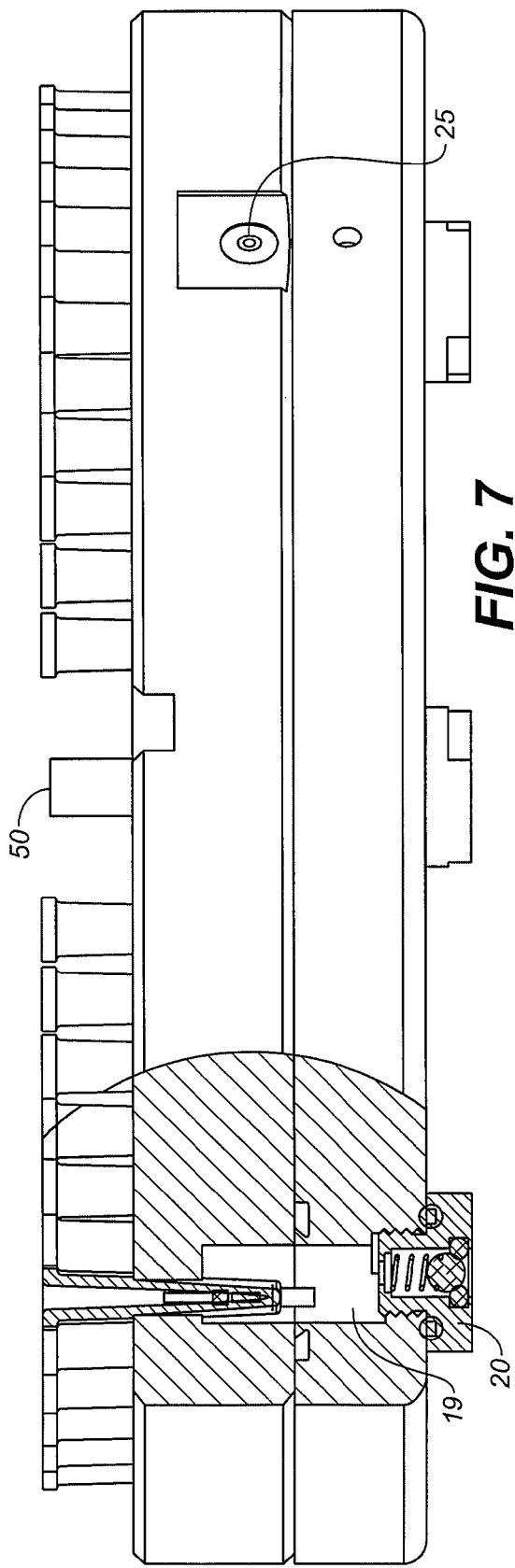
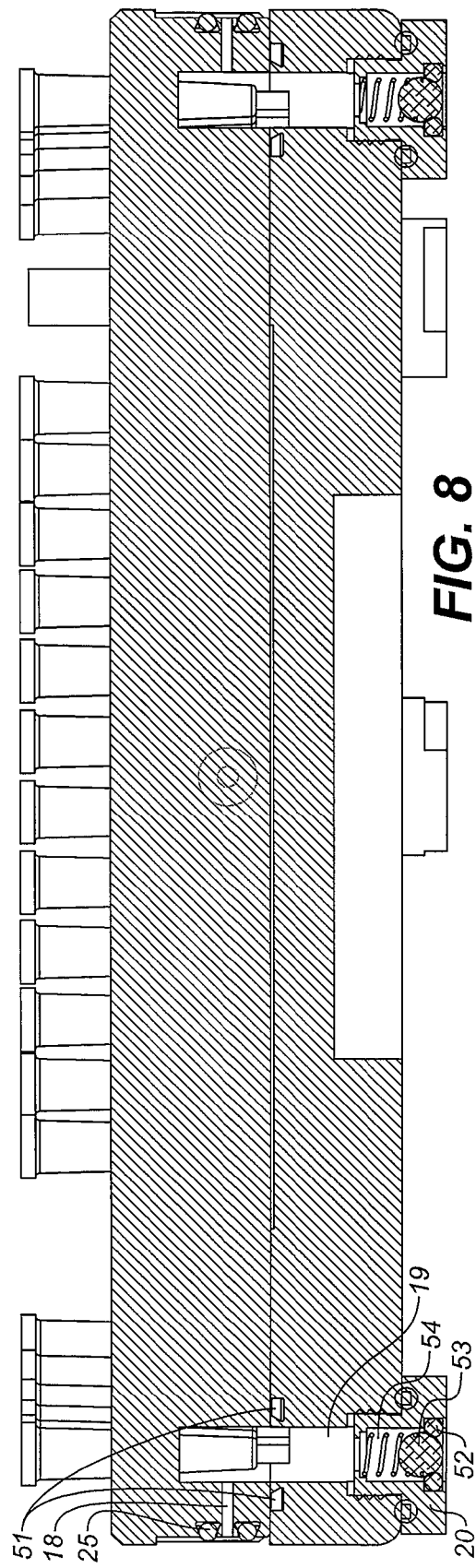
FIG. 7
FIG. 8

SYSTEM FOR CONTROLLING AND OPTIMIZING REACTIONS IN SOLID PHASE SYNTHESIS OF SMALL MOLECULES

TECHNICAL FIELD

This invention relates to instruments for control over the reactions performed during the synthesis of small molecules when using solid phase synthesis chemistry.

BACKGROUND

Solid phase synthesis of small molecules has been performed for many years. The instrumentation used to perform the solid phase synthesis chemistry varies in design based on the type of synthesis and the scale of synthesis to be performed. Very early instruments were completely enclosed and were capable of synthesis of only small numbers of different molecules in a single synthesis run. The consumption of reagents of these instruments was very inefficient. They consumed too much reagent and took too much time to make them viable for synthesizing the growing need for more different molecules to be produced in shorter time and at a lower cost.

As the scientific community developed processes that called for larger and larger numbers of different molecules, the molecules had to be synthesized faster and at a lower cost.

Instruments were developed to produce larger numbers of different molecules in a single synthesis run. A design that incorporated open ended reaction vessels (typically called columns or wells) allowed more economical synthesis of larger numbers of different molecules. This general design has been used in various instruments in more recent years. However this design has always been implemented with relatively inefficient control over the reaction process because reagents are moved through the reaction vessels using only one mechanism, namely gas pressure from above. In one common usage the reaction vessels have an open top and an open bottom. Between the open top and open bottom is a solid support material held in the solid support by a top filter and a bottom filter. Such a reaction vessel is held in a holder in which the open top end is held in a first area and the open bottom end is held at a second area. The only flow between the first area and the second area is through the reaction vessel. Once liquid is dispensed into a reaction vessel, the liquid can act as a plug in the reaction vessel as it moves through the reaction vessel. The only way to equalize the pressure between the first area and the second area is to migrate the liquid through the reaction container. By using one gas pressure from one gas pressure source and one drain in a chamber holding a plurality of reaction vessels, liquid is drained from the reaction vessels at only one flow rate. This is not ideal for optimization of reactions.

One result is that the reagents move through the reaction vessels too quickly. This in turn may require the addition of greater volumes of reagents. Since flow rate through the reaction vessel can be controlled only in a limited manner, additional reagent is used to ensure that sufficient reagent will react on the solid substrate. A considerable amount of reagent may flow through a reaction vessel without adding to the product being synthesized. These systems waste reagents, time and process gas that drives the reaction reagents through a solid phase.

The scientific and commercial community has continued to increase its need for larger and larger numbers of different synthesized molecules. There is pressure in the market to produce these molecules at lower cost. One means of achieving this lower cost is by making the synthesis process more efficient.

For open ended reaction vessels, reagents are dispensed into the open top of reaction vessels. The reaction vessel have open bottoms so reagent can be forced out the bottom of the reaction vessels. In between the open top and open bottom is a solid phase material where reactions take place. Reactants adhere to this solid phase. At the end of the reaction, an eluting reagent is added to remove the reaction products from the solid phase. These reaction products are collected in a collection container, such as a multiwell plate.

It is an objective to provide a more efficient system and method for production of solid phase synthesis reaction products.

SUMMARY

In present solid phase reaction systems, reaction vessels are held on a rotor. The open top ends extend from the top of the rotor and the open bottom ends are contained with one or more sealed chamber within the rotor. Reagents are dispensed into the reaction vessels. Gas pressure is then introduced, but the enclosed area above the rotor must be equalized with the sealed camber within the rotor. This is achieved by allowing gas to flow through the reaction vessels until the pressure is equalized. However, this will rapidly drive the fluid through the reaction vessel wasting costly fluid. To drain the sealed chamber, a drain is opened. Such a drain will drain the chamber at a single speed. This may not produce the flow rate through the reaction vessels that is most efficient. Utilization of both the process gas and the reaction reagents is not ideal.

The various embodiments of system and methods relate to a solid phase synthesizer reaction system. This type utilizes a number of flow through reaction vessels, each reaction vessel having an open top to allow introduction of reagents through said reaction vessel, an open bottom of each reaction vessel to allow liquid to flow from said reaction vessel and a solid phase reaction material within each of said reaction vessel between said open top end and open bottom end. Such systems use a rotor that holds a number of reaction vessels. These may be grouped into banks. A cover is positioned above the rotor, enclosing an upper sealable chamber. This is considered the "upper chamber" because it contains open tops of the reaction vessels. Within the rotor is a lower chamber that holds the open bottom ends of the reaction vessels. In some embodiments, multiple lower chambers are used. Each lower chamber includes a passageway through the rotor, allowing gas communication between the upper chamber and the lower chamber. When the area around the rotor is pressurized, in prior systems, the only pathway to the lower chamber would be through the reaction vessel. The present embodiment, this passageway through the rotor allows equalization of the pressure between the upper and lower chambers without flow through the reaction vessels.

The "upper chamber" will include both the area above the open top of the reaction vessels, and the area between the gas source and reaction vessels. This may include some area around the rotor. The rotor may include a priming port that flows to a drain.

In one embodiment, this passageway through the rotor into the lower chamber is part of a second drain system that connects to tubing and valve elements to allow variable speed draining of gas from the lower chamber. A first drain system at the bottom of the sealable lower chamber is a more rapid speed drain of both gas and liquids. In one embodiment, this first drain is a ball check valve. This in turn, allows greater control of the flow rate through reaction vessels, allowing more efficient reactions by regulating the flow rate of reagents through a solid support material. In one embodiment, this variable speed drain includes a manifold attached to multiple calibration tubes, each of which is controlled by a valve. When one valve is opened, gas can flow through a calibration tube, through the manifold, and through the tube connecting this drain to the lower chamber. This provides a simple, low cost device which still greatly optimizes the flow through the reaction vessels. In one embodiment, the first drain, as a variable speed drain, drains gas at a lower rate and the second drain drains both liquid and gas at a rate that is, for example, two to one hundred times greater. By activation of the different drain systems, a user is allowed control of the flow rate through the reaction vessels and a more rapid drain to clear both reaction vessels and the lower chamber of liquid. In one embodiment, the variable rate drain is not in line with the longitudinal axis of the reaction vessels.

In one embodiment, the cover over the rotor will hold a number of reagent dispense nozzles. A motor linked to the rotor allows the rotor to be turned such that various reagent dispense nozzles align with the open top ends of the reaction vessels. The motor is mounted on a motor mount. In one embodiment, this motor mount includes a spill channel that collects spilled waste and a drain to drain this spill channel, preventing spills from compromising the motor or other sensitive system elements.

To reduce the requirement of process gas, in one embodiment a spacer is used on top of the rotor. This reduces the amount of gas that fills the space between the rotor and the cover that encloses the rotor into an interior space.

In one embodiment a method of fluid control is described. This method utilizes the above described system embodiments. In this method, pressure is equalized between the sealable interior chamber where the reaction vessels terminate, and the area surrounding the rotor where the open top ends of the reaction vessels terminate without requiring that the entire flow move through the reaction vessel. This reduces the flow through the reaction vessels to a minimal level (gravitational flow). A variable rate drain can then be opened, to allow a selectable flow rate of liquid reagent through the reaction vessel.

BRIEF DESCRIPTION OF THE DRAWINGS

FIG. 7 is a side perspective view of FIG. 6 showing the chamber formed at the outlets of the reaction vessels.

FIG. 8 is a cross sectional view of the chamber shown in FIG. 7. The sealable vent hole is detailed.

DETAILED DESCRIPTION

Figure 1:
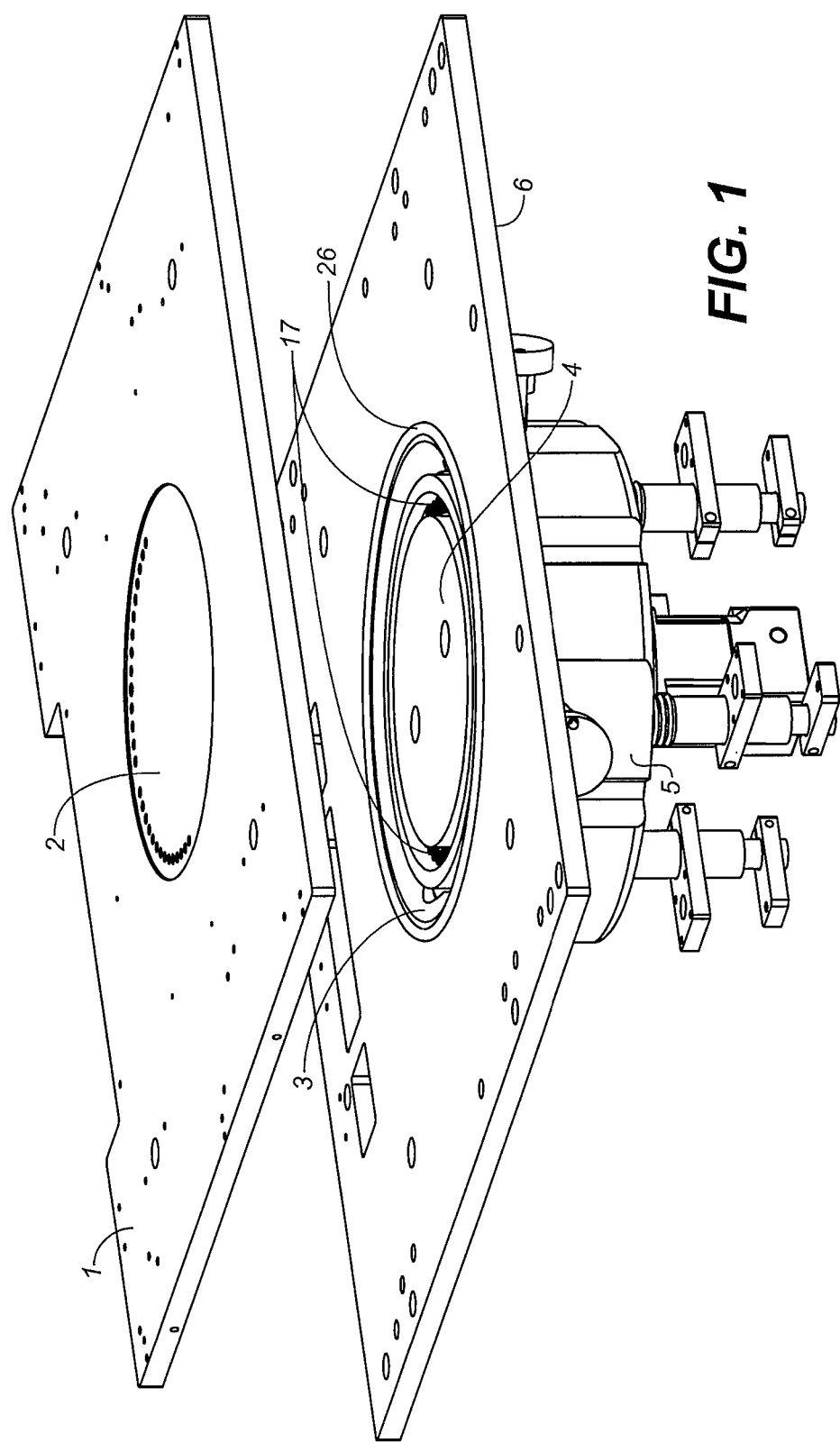
FIG. 1 is a top perspective view of the sealable reaction vessel inlet chamber with the reaction vessel holder installed. The top of the sealable chamber is shown in the open position.

With reference to FIG. 1, an exploded view shows a top plate 1 and a top window 2. Top plate 1 is hinged or fixed to a frame (not shown) such that it is movable by the operator to allow access to reaction vessels 17. During operation top plate 1 is bolted or clamped onto a lower plate 6 forming a leak proof seal between top plate 1 and lower plate 6 at O-Ring seal 26. Top plate 1 and lower plate 6 are contained within a housing (not shown). Rotor 4 in lower plate 6 is shaped to define a sealable upper chamber 3. The reaction vessels 17 are held in the sealable upper chamber 3. The rotor 4 is housed on bowl 5.

Figure 2:
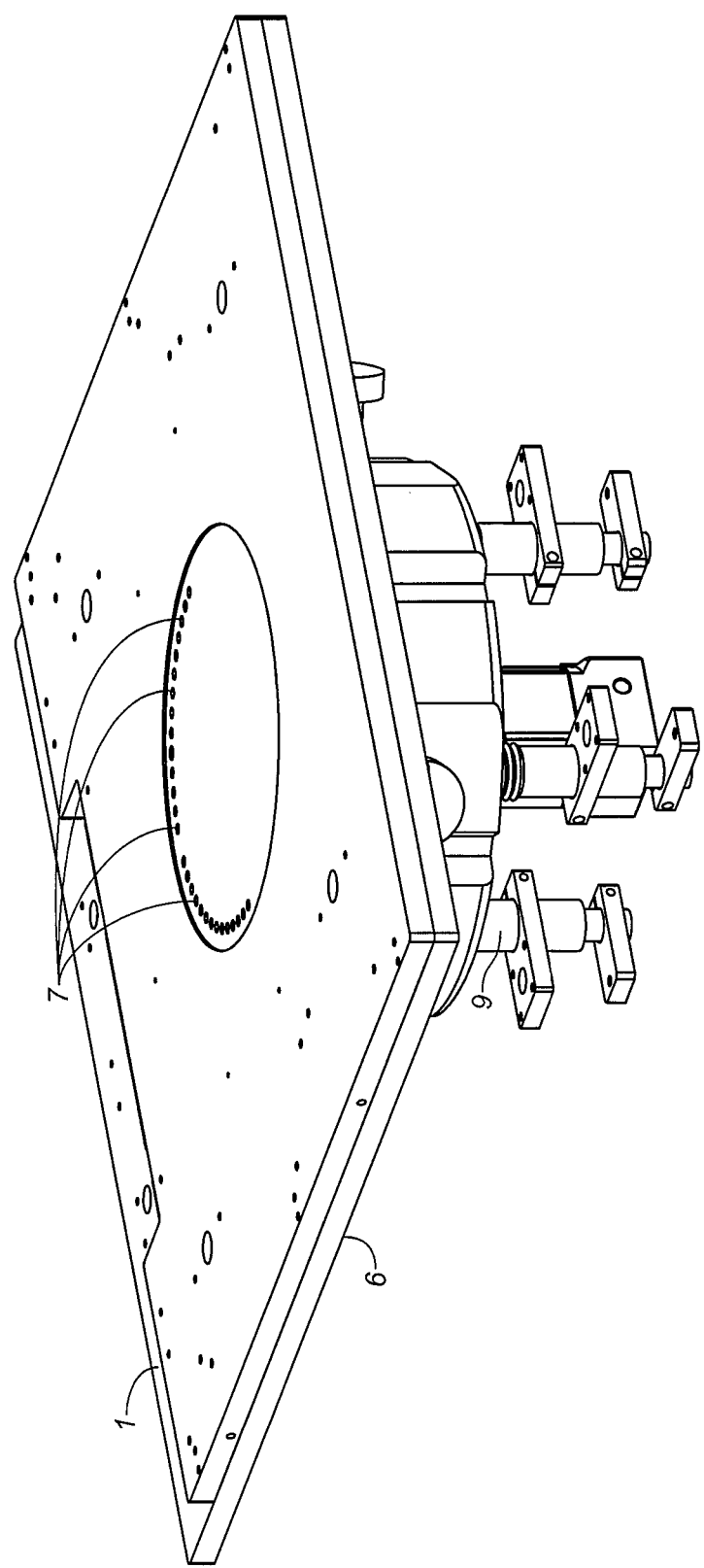
FIG. 2 is the view of FIG. 1 with the top of the sealable chamber shown in the closed position.
Figure 5:
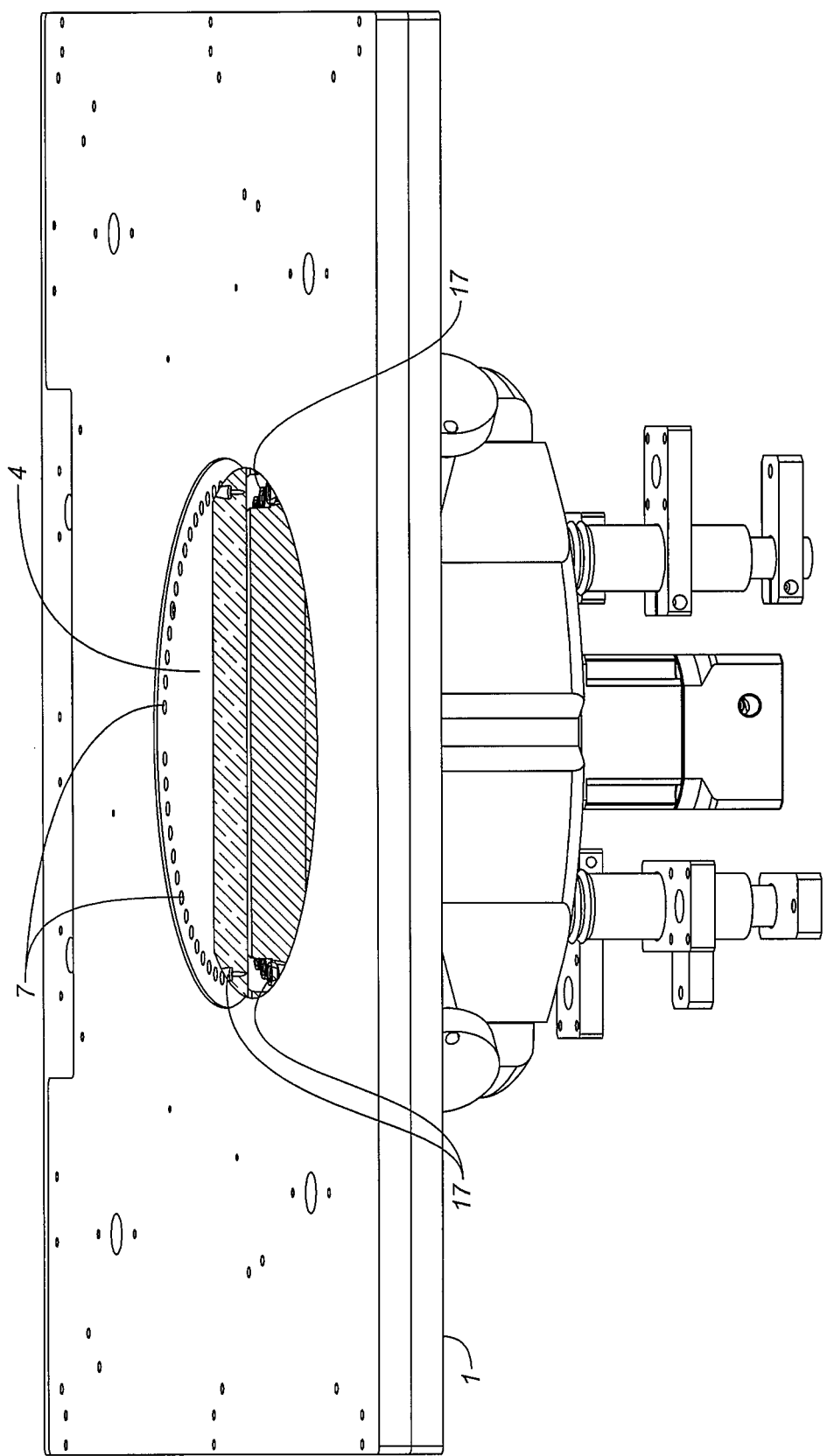
FIG. 5 is a top perspective detail of the sealable reaction vessel inlet chamber with the rotor installed. The top of the chamber has the reagent dispensing nozzles mounted in it (dispensing nozzles not shown).

As shown in FIG. 2, top plate 1 is bolted onto to lower plate 6. Mounted on top window 2 are reagent dispense nozzles 7, as seen in FIG. 5. Rotor 4 may be rotated to position reagent dispense nozzles 7 above reaction vessels 17. Dispense nozzles are stationary, held on top cover 2.

Figure 3:
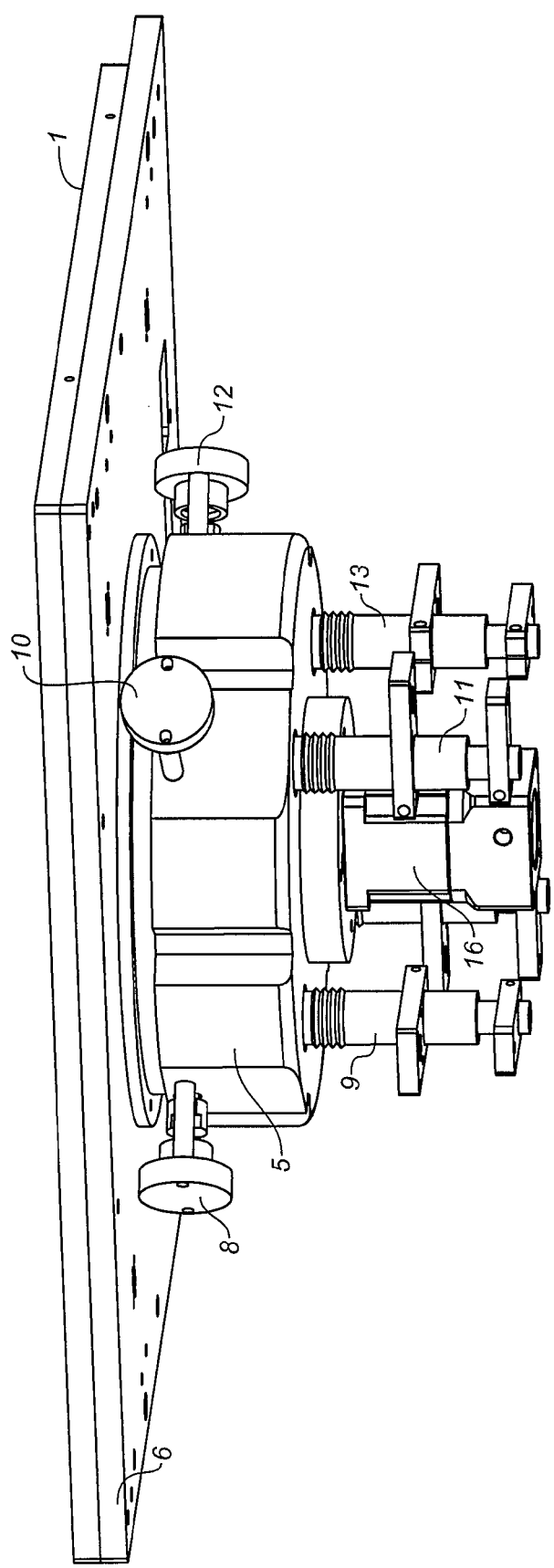
FIG. 3 is a side view of FIG. 2 showing three of the four drain stations.
Figure 4:
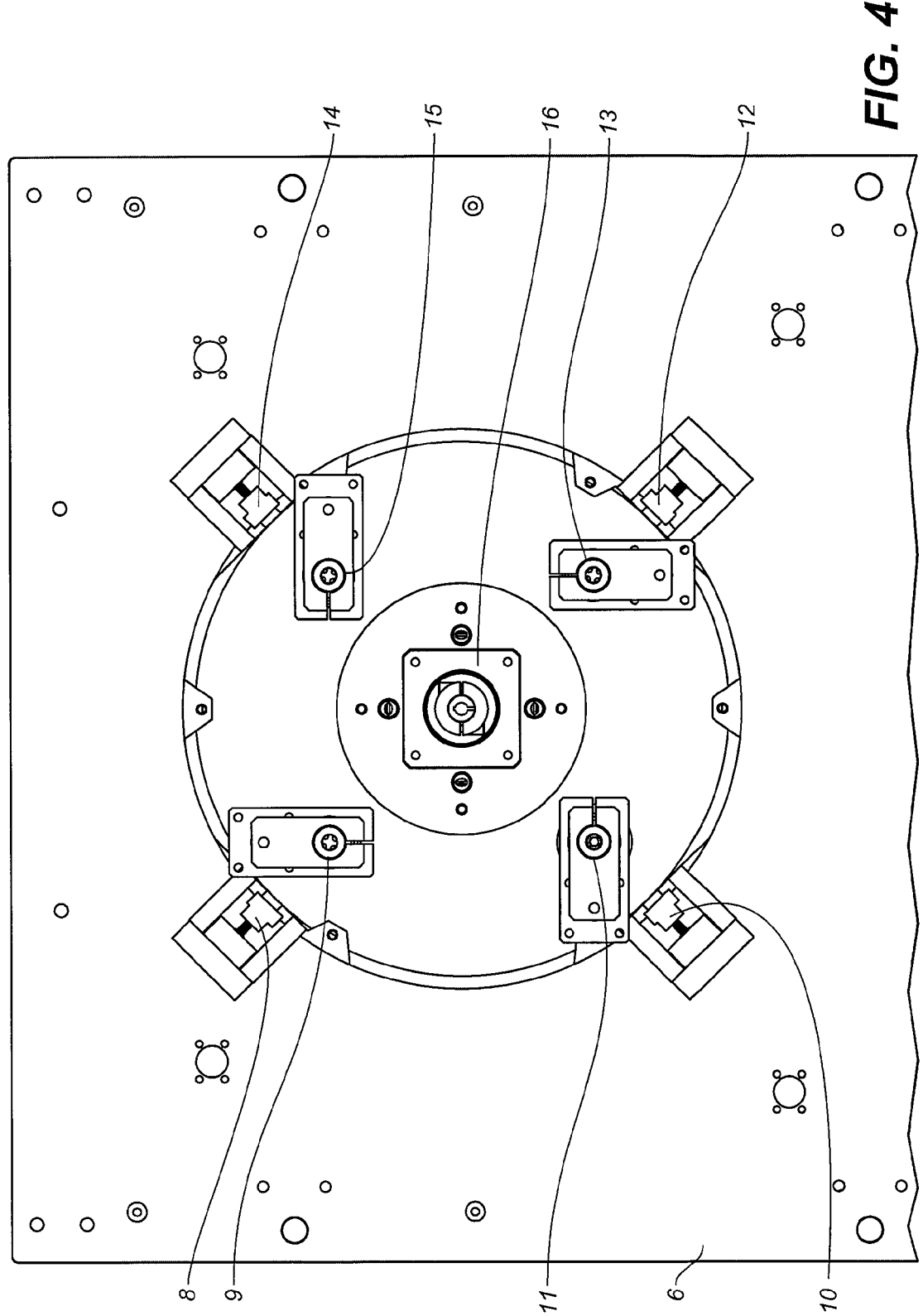
FIG. 4 is a bottom view of FIG. 3, showing all four drain stations. Each drain station has 2 waste connection ports.
Figure 9:
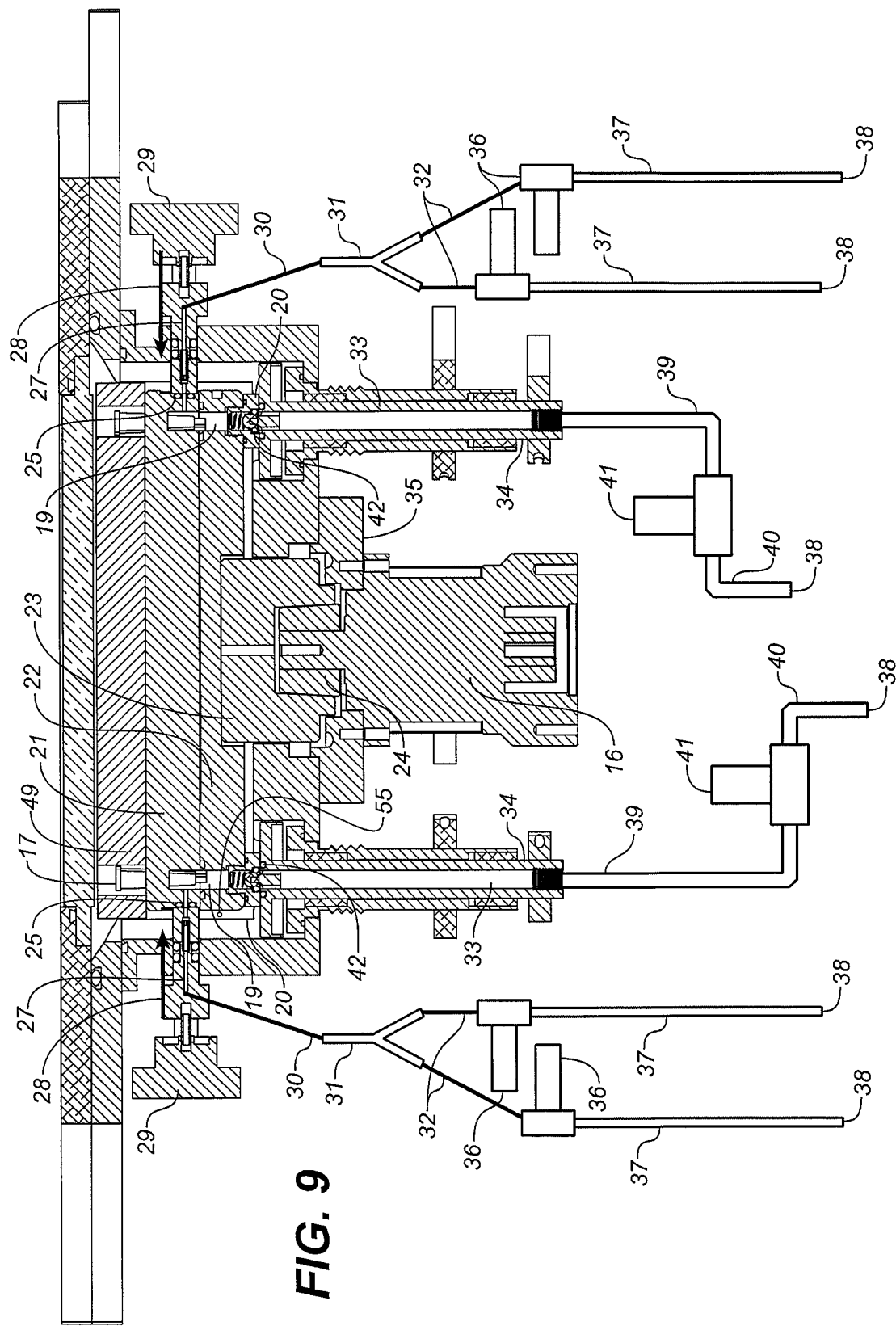
FIG. 9 is a cross section of FIG. 3 showing the rotor mounted in the chamber and 2 of the 4 drain stations completely plumbed.

With reference to FIGS. 3 and 4, bowl 5 holds drain stations 8, 9, 10, 11, 12, 13, 14 and 15. As explained below, drain stations have components that make up the high flow waste system and the variable flow waste system. Also mounted centrally on plate 6 is motor system 16. This system includes a motor, a gear box, an encoder, a home sensor, a motor drive controller, and a power supply. The rotor is coupled to motor system 16 through hub 23 and collet 24 (as shown in FIG. 9), allowing rotation and positioning of the rotor. This allows selective placement of the reaction vessels 17 below a selected dispense nozzle 7. This is controlled by an automated control system utilizing a programmed computer and software (not shown).

Figure 6:
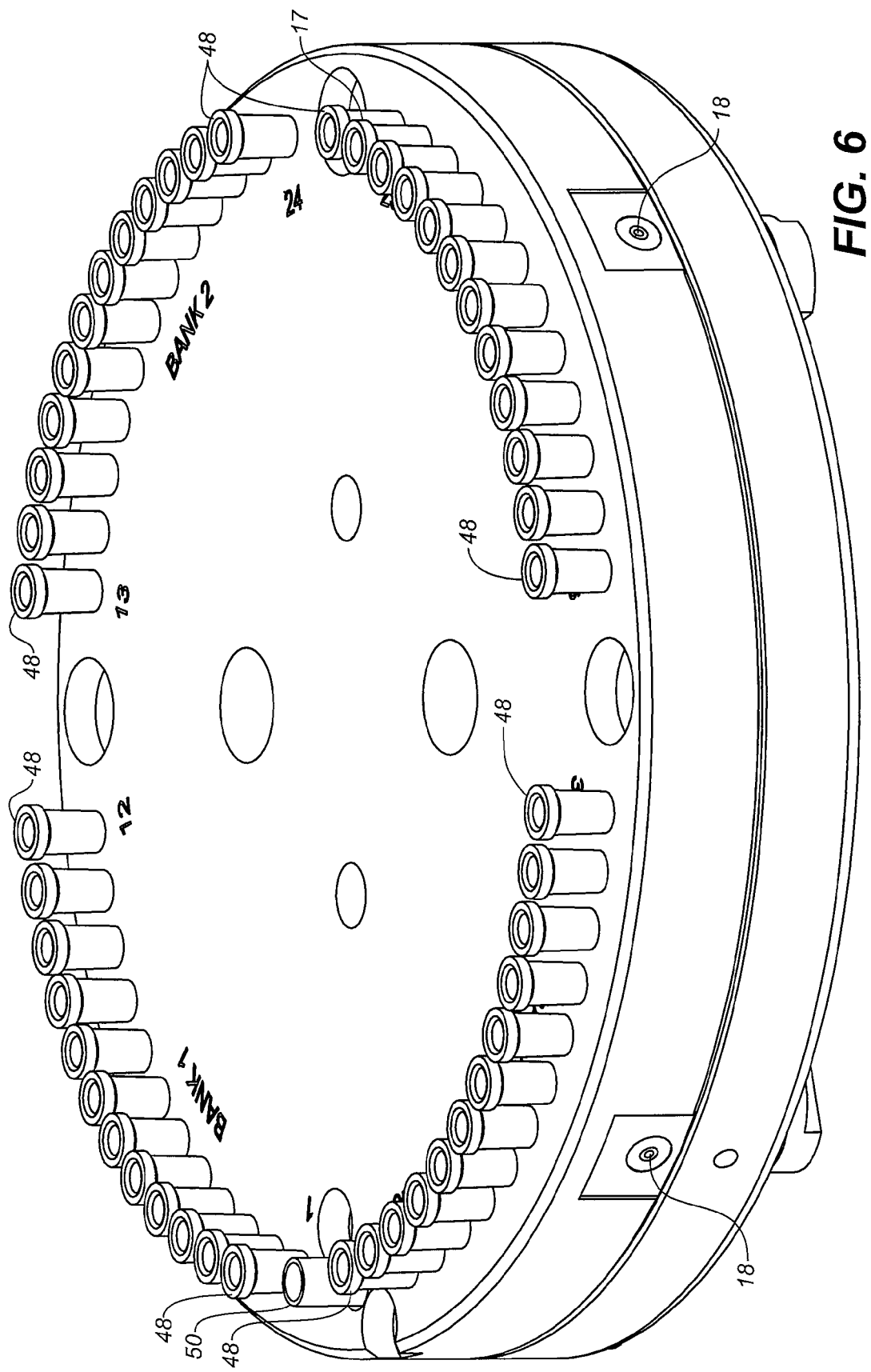
FIG. 6 is a top perspective view of the rotor showing a sealable vent hole into each bank lower chamber.
Figure 7A:
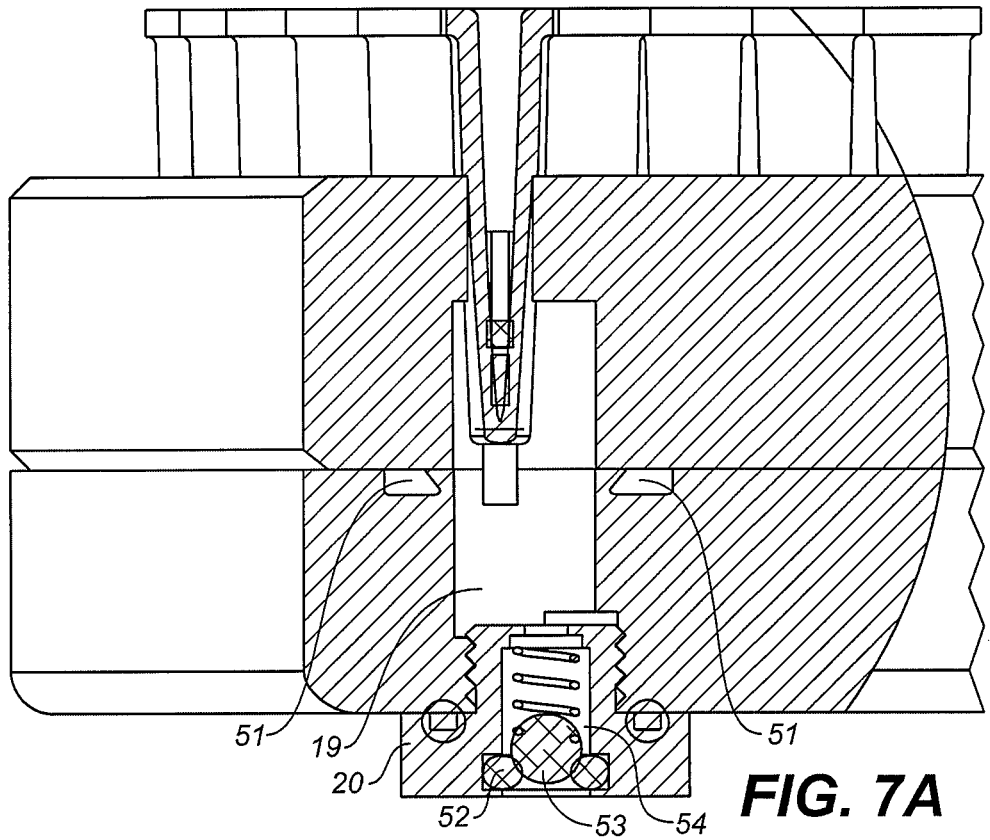
FIG. 7A is a cross sectional detail of the drain shown in FIG. 7.

With reference to FIGS. 6, 7 and 7A, the rotor is shown divided into banks 48 for holding groups of reaction vessels 17. These are enclosed to form upper chamber 3.shown in FIG. 1. As shown, 12 reaction vessels 17 are grouped in each bank 48. In alternative embodiments, more or fewer reaction vessels or banks could be used, depending on need and available space (rotor size).

A vent port 18 selectively sealed to hollow shaft 27 by a seal 25 is used with each bank. Vent port 18 extends from a sealable lower chamber 19 to a passage connecting to sealable upper chamber 3. A priming port 50 is also used to dispense reagents to waste while bypassing all reaction columns. A single priming port is used for the rotor. A partial cutaway view shows the high flow waste system check valve 20 which allows draining of the sealable lower chamber 19. The open bottom ends of the reaction vessels 17 extend into this lower chamber 19. Each of bank 48 has its own high flow waste system check valve 20 that drains one lower chamber 19. Each of the lower chambers 19 are isolated from each other. When reaction vessels 17 are installed in the rotor 4, the lower chambers 19 and the upper chamber 3 (shown in FIG. 1) are separated by the reaction vessels 17. The vent ports 18 are also associated with each bank 48 of reaction vessels 17. These vents serve two purposes. First, they provide an alternative means by which the upper chamber 3 and the lower chamber 19 can be connected during gas flow. This allows regulation of pressure between the upper chamber and the lower chamber, which stops the flow in both directions through the reaction vessels which would result from pressure equalization between the upper chamber and the lower chambers. Second, vent port 18 may be connected to a variable flow waste system. This allows liquid to flow through the reaction vessels at selectable different flow rates.

As described, pressure the described embodiments allow the pressure source that pressurizes the upper chamber to also pressurize the lower chamber. It should be realized that this can work in the opposite way: the passageway between the upper and lower chamber can be used to relieve pressure from the lower chamber. It is equally beneficial to have a mechanism to release the pressure in the lower chamber. It is not optimal for gas pressure in the lower chamber to flow up through the reaction vessels. In the disclosed embodiments, the same vent hole allows both vent the lower chamber and pressurizing it.

If gas flows up through the reaction vessels, reagent expelled into the lower chamber from multiple reaction vessels, all of which may have different reagents in them, may also flow into the reaction vessels. These reagents can be drawn back up through the reaction vessels causing cross contamination between reaction vessels. In the disclosed embodiments, the system allows venting the lower chamber through the port on the side of the rotor (one for each bank). This substantially eliminates cross contamination due to reverse flow through the reaction vessels.

Figure 8A:
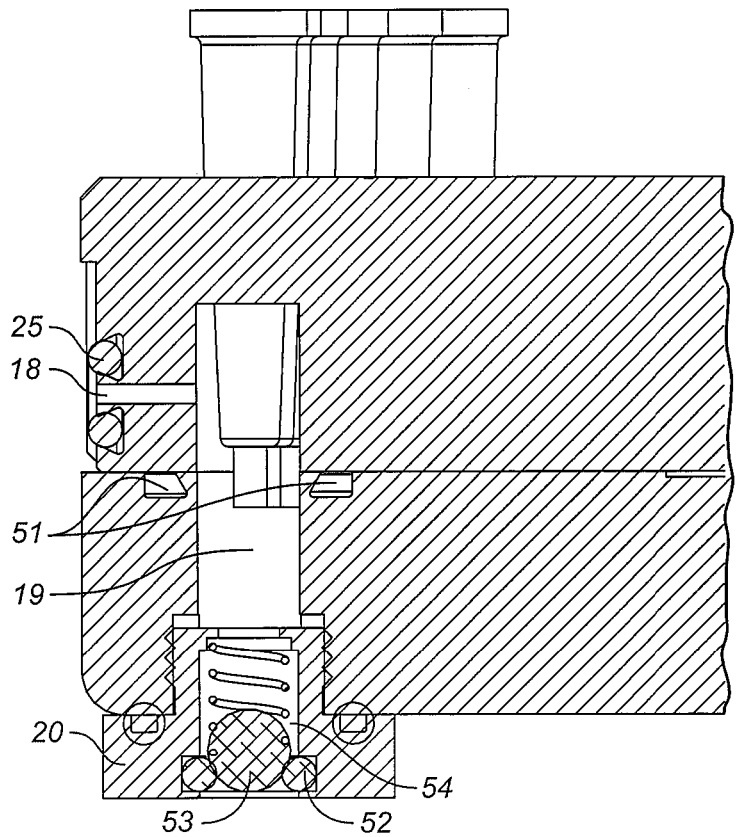
FIG. 8A is a cross sectional detail of the drain shown in FIG. 8.

With reference to FIGS. 8 and 8A, lower chamber 19 is shown in this cutaway having a port 18 covered by a seal 25. An O-ring seal 51 between the rotor top half 21 and the rotor bottom half 22 form a pressure tight seal for each bank 48 in the rotor 4. Also shown is high flow waste system drain check valve 20. Each high flow waste system drain check valve 20 illustrated in these embodiments utilizes a ball valve in which a ball 53 is biased by a spring 54 and retained against an O-ring 52.

Tubing inside diameter (ID) and length of the high flow waste system and the variable flow waste system is selected to achieve the flow rate difference between the High Flow Waste Systems and the Low Flow Waste Systems. In one example, one quarter inch OD×$\frac{3}{16}$ inch ID tubing was used on drain of the High Flow Waste System, where the ball is biased against the drain opening.

The cross section of FIG. 9 shows a number of the major systems including:

The Rotor

The rotor 4 is driven by the motor 16, allowing circumferential positioning of the reaction vessels 17. The rotor consists of the top spacer 49, a reaction vessel holder 21 and a rotor bottom 22. Reaction vessel holder 21 and rotor bottom 22 are bolted together, and top spacer 49 is placed into position and is located using a locating pin (not shown) or other means. The top spacer minimizes the space required for the sealable upper chamber. It extends proximate to window 2 with the exception of the area above the reaction vessels 17. The reaction vessel holder 21 includes a number of grouped holes that the reaction vessels 17 extend through. The area surrounding the rotor assembly is the sealable upper chamber 3 and the area between rotor part 21 and rotor part 22 is the sealable lower chamber 19. Upper chamber 3 includes the area above and around the open top end of the reaction vessel 17. It also include the rest of the space connecting this chamber to the gas source. As indicated, this includes the passageway on the side of the rotor, the space on the top of the rotor between the cover 2 and the spacer 49, and other space around the rotor. The rotor 4 includes one or more banks of the sealable lower chambers 19 for each bank of reaction vessels 17. The sides of rotor reaction vessel holder 21 include one port 18 and seal 25 for each bank of reaction vessels.

Rotor Rotation

As noted, motor 16 turns rotor. Part of motor 16 is an encoder, allowing rotational positioned to be determined. This allows the rotor to position the reaction vessels below a nozzle for reagent dispensing. The rotor can also be selectively positioned such that the port 18 having seal 25 is brought into a position to allow sealed connection with the center passage of shaft 27. Rotor hub 23 is an interconnection mechanism to connect rotor 4 to the transmission shaft. Collet 24 is also part of the connection mechanism between the transmission shaft and rotor 4. In one embodiment, the rotor is bolted onto the connection mechanism.

Dispensing of Reaction Reagents

Reactions occur on a solid support located within reaction vessels 17. As explained with regard to FIG. 1, the dispense nozzles 7 are aligned with open top ends of reaction vessels 17 held on rotor 4. Reagents may then be dispensed into the reaction vessels 17.

Control of Flow Rate through the Reaction Vessels

A mechanism that includes pneumatic cylinders, hollow shafts, solenoid valves, calibrated tubing and manifolds is used to selectively engage the rotor to connect the desired calibrated tube from the reaction vessel outlet chambers to waste. This system is referred to as the "variable flow waste system".

Control of flow rate during the reaction is controlled by a variable flow waste system. In this system pneumatic cylinders 29 are engaged to move hollow shafts 27 horizontally to connect or disconnect the center passage of hollow shaft 27 with port 18 on the rotor 4. This is indicated by arrow 28. Tube 30 connects the center passage of the horizontal hollow shaft 27 to a manifold 31. Each port on the manifold is connected to a calibration tube 32 which in turn connects to a two way solenoid valve 36. Two way solenoid valves connect to tubes 37 which connect to waste 38. Each variable drain station has one set each of these components. The system as illustrated thus would have four variable drain systems, one for each bank of reaction vessels. This mechanism would allow the passage of gas from the lower sealed chamber to the upper sealed chamber. Each of the valves and pneumatic cylinder are able to operate separately under automated control.

In one embodiment the calibration tubes 32 include a first tube of 1/16inch OD×0.020 inch ID and a second tube of 1/16 inch OD×0.0155 inch ID. These can be used as alternative pathways for this drain, or could both be used together. This provides three different drain rates.

In one embodiment the system uses a fixed pressure. The pressure may be in a range from 2 psi to 7 psi. In one embodiment, the pressure using currently available commercial solid supports was 3 to 4 psi (for example 3.5 psi).

High Flow Waste System to Rapidly Drain Reaction Vessels

A mechanism that includes pneumatic cylinders, hollow shafts, tubing, solenoid valves and pneumatic valves is used to selectively engage the rotor and quickly remove all waste reagents from the reaction vessels and the reaction vessel outlet chamber and send waste reagent to a vented waste container. This system is referred to as the "High Flow Waste System".

When the reaction is complete and it is desired to drain the reaction vessels and the lower chamber, hollow shaft 34 is moved in the direction of arrow 33. A tip on the end of shaft 34 displaces the ball of the rapid flow check valve 20. The components of this valve where discussed in respect to FIG. 8. The liquid and gas in the lower chamber 19 flow into hollow shaft 34 and into tube 39 when valve 40 is opened. The liquid then flows into tube 41 and to waste.

For a given pressure the High Flow Waste System is designed to flow at a rate that is at least several times to about 100 times that of the variable flow Waste Systems. In one embodiment, a pressure value is chosen that will allow the High Flow Waste System to empty all reaction vessels and reaction vessel outlet chambers within 2 seconds.

Figure 10:
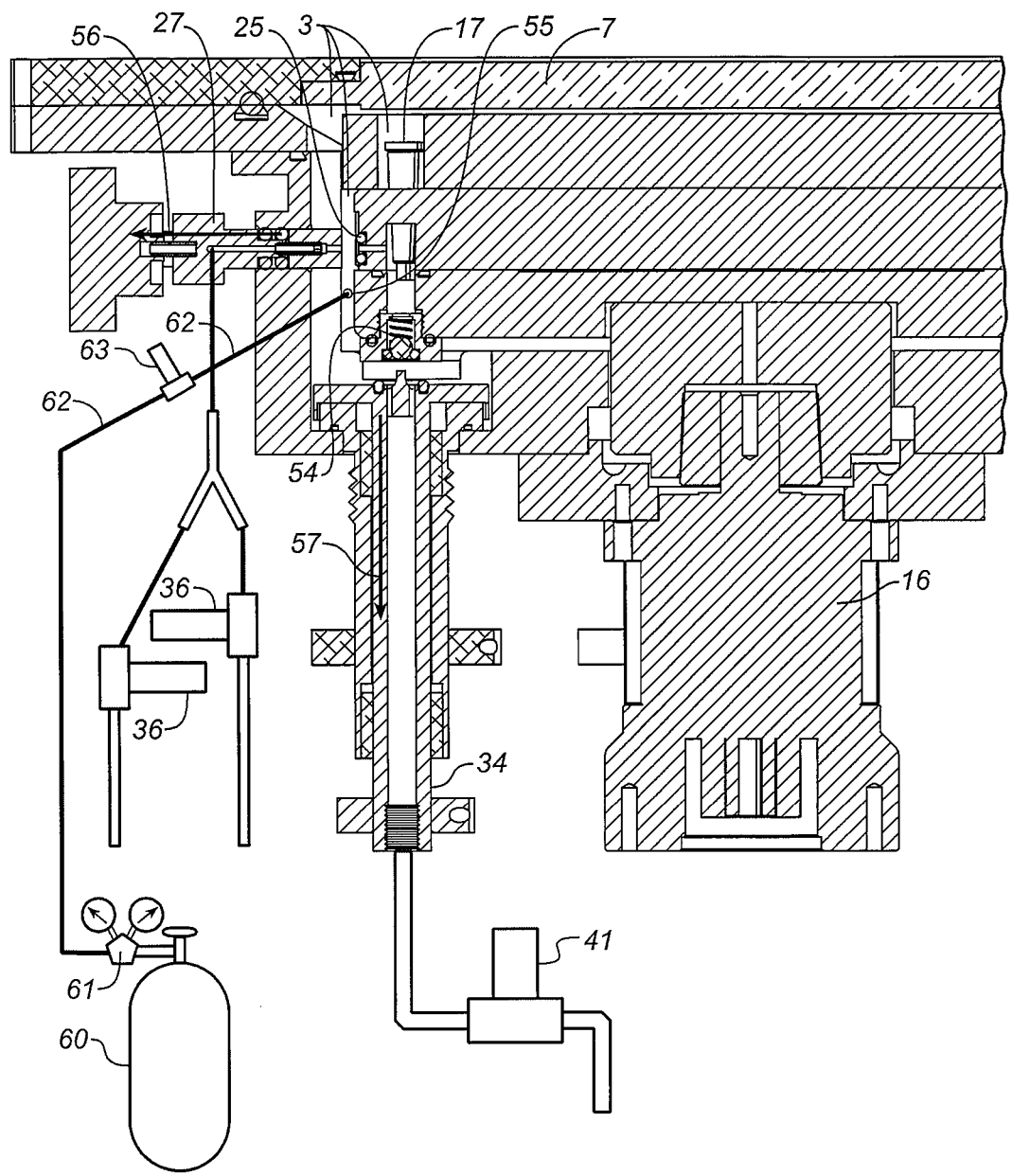
FIG. 10 is a cross section of part of FIG. 3, showing one of the waste stations shown in FIG. 9. The bank vent hollow shaft is shown disengaged from the rotor and the fast drain shaft is also shown disengaged from the rotor. The external gas source, valves and tubing are shown in this figure however they are not cross sectioned.

The initial positioning of elements is shown in FIG. 10. The following description occurs for each of the lower chambers in the rotor. If each lower chamber is provided with a high flow rate waste system and a variable flow rate waste system, the process described occur simultaneously for each of the lower chambers in the rotor. Horizontal shaft 27 is moved to the disengaged position indicated by arrow 56. Shaft 27 is thus positioned so that it does not engage rotor 4. The vertical drain shaft 34 is moved to the down position indicated by arrow 57. In this position drain shaft 34 does not engage with rotor 4. Solenoid valves 36 and 41 are closed, so there is no flow in the connected pipes. Rotor 4 may then be rotated by motor 16 such that a selected dispense nozzle 7 is positioned above the open tops of reaction vessel 17. A separate system for dispensing reagents using pressurized reagent containers, valves, and tubing connected to the dispense nozzles 7 is conventional and known in this art.

After the reagent has been dispensed, rotor 4 is rotated to align the sealed lower chamber with the drains of the variable flow waste system. As noted, each of the banks of reaction vessels is separately sealable and have a high flow rate drain and a variable flow rate drain. Upper chamber 3 is pressurized with inert gas through delivery port 55. The lower chamber 19 is also pressurized via port 18. The reagent dispensed into the top of reaction vessel 17 will not flow out of the bottom of reaction vessel 17 because the pressure on the reaction vessel 17 inlets and the reaction vessel 17 outlets is equal. Flow will result only from the liquid pressure head exerted by the liquid dispensed into the open tops of the reaction vessels which is negligent given flow restrictions found within common use reaction vessels.

Figure 11:
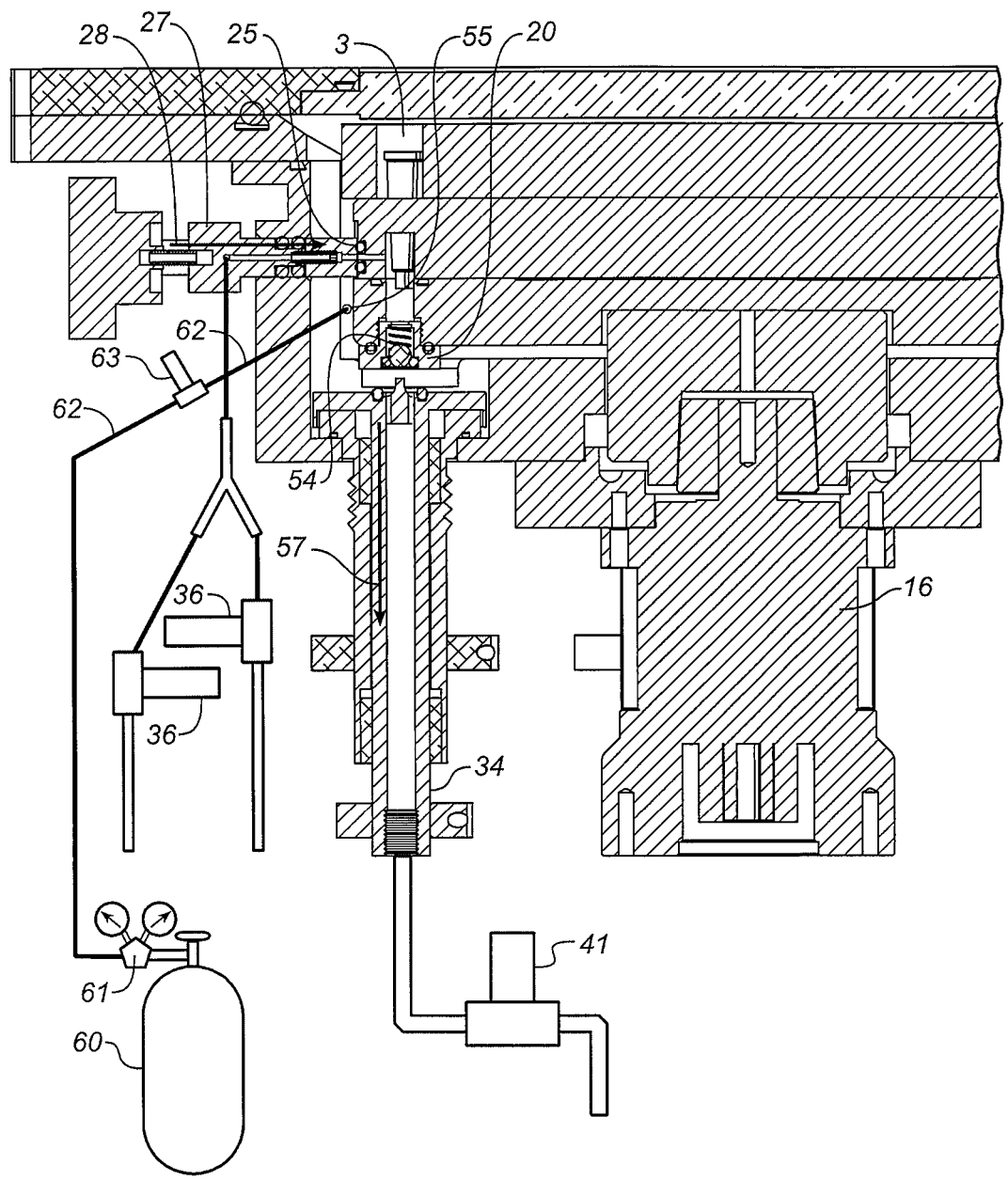
FIG. 11 is a cross section of part of FIG. 3, showing one of the drain stations shown in FIG. 9. The bank vent hollow shaft is shown engaged with the rotor thereby connecting the reaction vessel outlet chamber for one bank to the hollow shaft and subsequently through a solenoid valve to waste. The fast drain shaft is shown disengaged from the rotor. The external gas supply, valves and tubing are shown in this figure however they are not cross sectioned.
Figure 12:
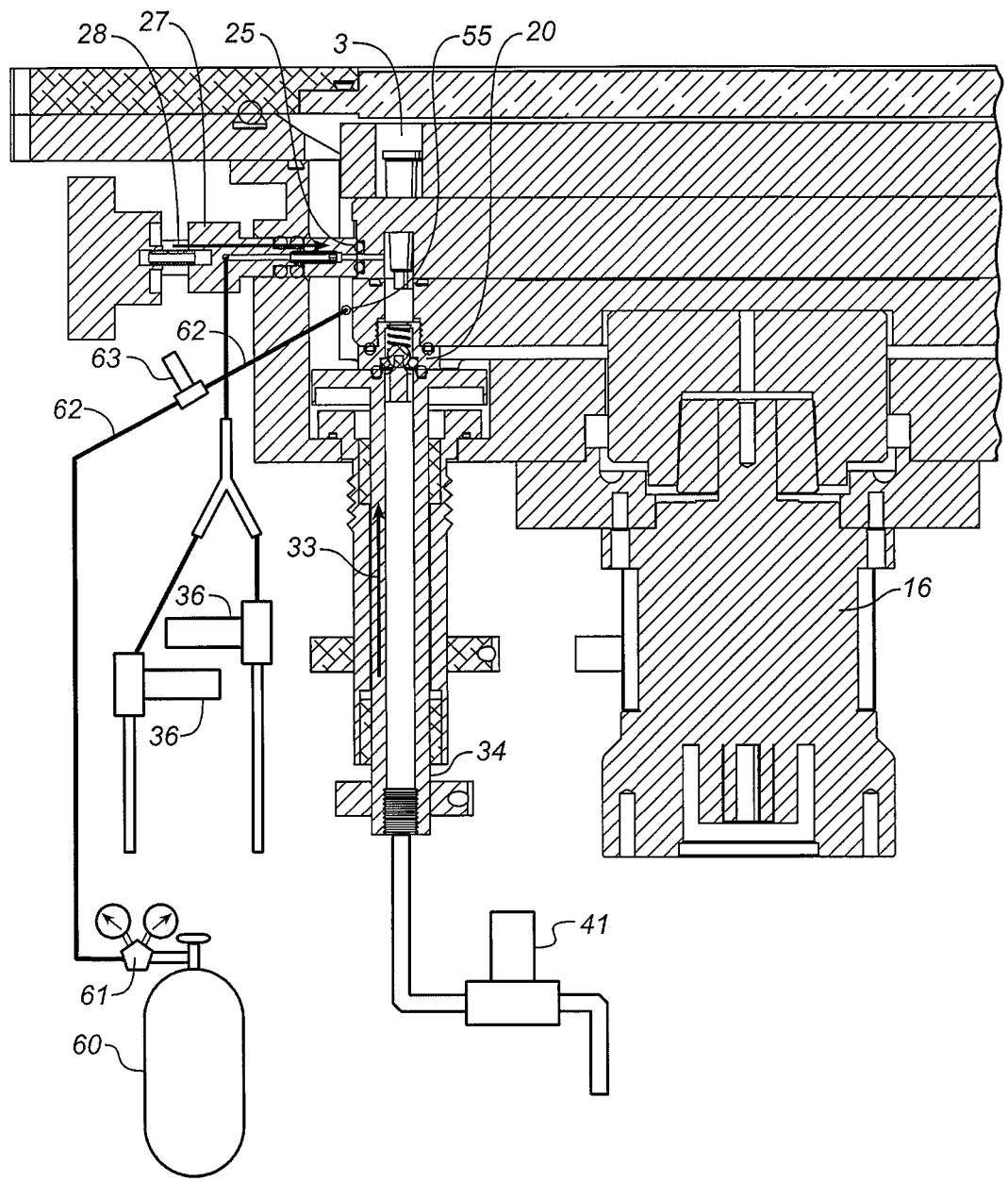
FIG. 12 is a cross section of part of FIG. 3, showing one of the drain stations shown in FIG. 9. The bank vent hollow shaft is shown engaged with the rotor thereby connecting the reaction vessel outlet chamber for one bank to the hollow shaft and subsequently through a solenoid valve to waste. The fast drain shaft is shown engaged with the rotor thereby connecting the reaction vessel outlet chamber for one bank to the fast drain hollow shaft and subsequently through a pneumatic valve to waste. The external gas source, valves and tubing are shown in this figure however they are not cross sectioned.

With reference to FIG. 11, the hollow drain shaft 27 is moved in the direction of arrow 28. The flow channel in the center of the horizontal shafts 27 is connected to port 18 and sealed by seal 25. One of the two way valves 36 is opened by the system controller, allowing gas to pass into tube 30, through manifold 31, into one of calibration tubes 32 and into one of tubes 37 and to waste 38. This creates a pressure differential between upper chamber 3 and lower chamber 19 for that bank of reaction vessels 17. The system controller will select the appropriate two way valve 36 to open based on the flow rate that is desired for the particular reaction vessel being used in a given bank of reaction vessels. Fluid will flow through the reaction vessel for a set time required for the reaction protocol. In the illustrated embodiment, either one of the two valves could open, or both valves could open. This provides three flow rates. More flow passages could be added to allow a greater number of flow rates. Alternatively, a different type of valve could be used to regulate flow rate.

Figure 13:
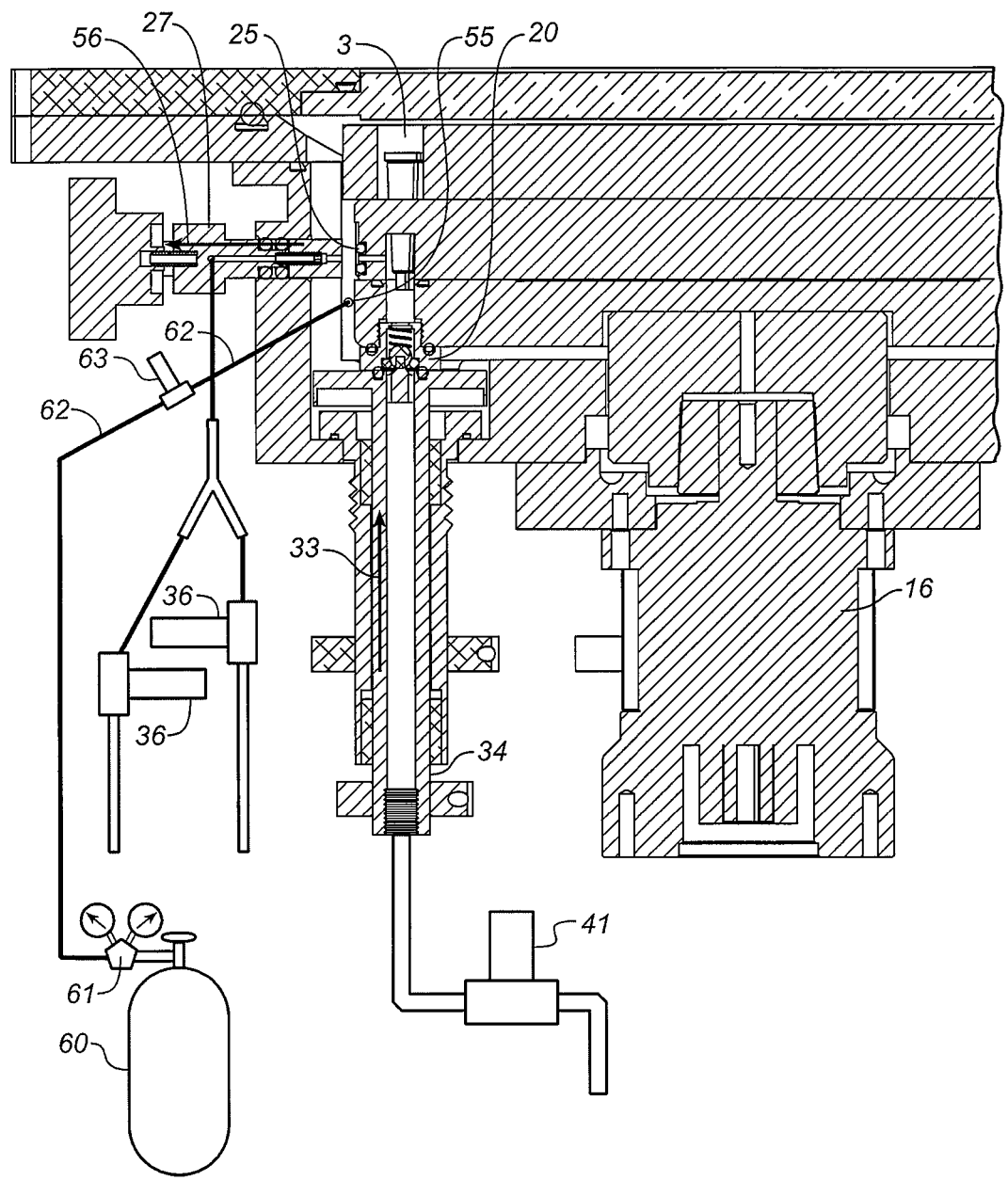
FIG. 13 is a cross section of part of FIG. 3, showing one of the drain stations shown in FIG. 9. The bank vent hollow shaft is shown disengaged from the rotor. The fast drain shaft is shown engaged with the rotor thereby connecting the reaction vessel outlet chamber for one bank to the fast drain hollow shaft and subsequently through a pneumatic valve to waste. The external gas source, valves and tubing are shown in this figure however they are not cross sectioned.

With reference to FIG. 13, flow to the variable flow waste system is stopped by closing valves 36 and activating pneumatic cylinder 29 to retract the shaft 27 such that port 18 does not connect to the hollow interior of shaft 27. This will prevent gas from flowing out through the variable flow waste system. At the time in the process when it is desired to quickly empty the reaction vessels 17 in a given bank Hollow shaft 34 is moved in the direction of arrow 33. This opens the ball check valve as discussed with respect to FIG. 8. The gas and liquid contents of the lower chamber 19 are drained into hollow shaft 34, into tube 39 when valve 41 is opened. The gas and liquid will then flow into tube 40 and go to waste.

Figure 14:
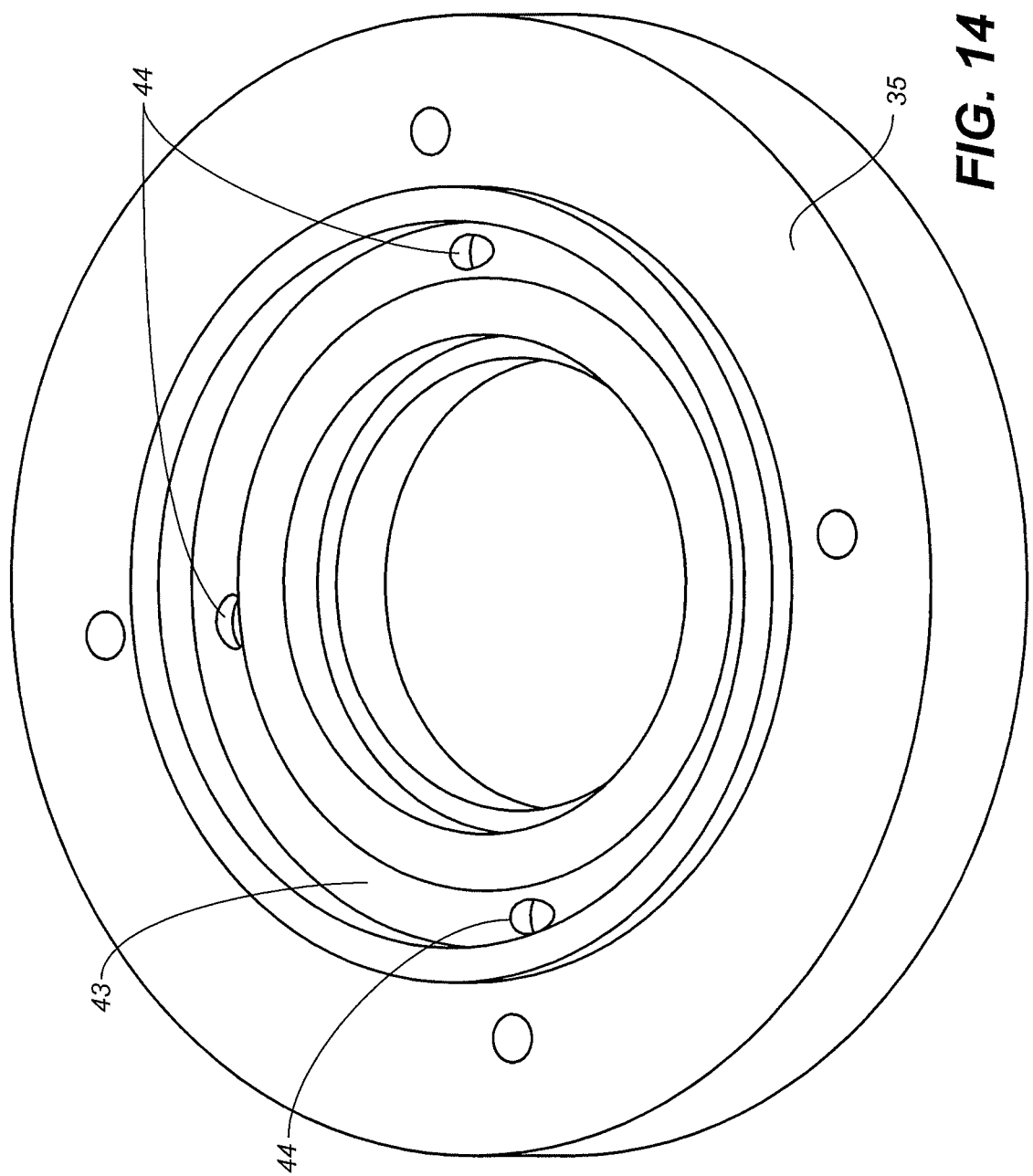
FIG. 14 is a top perspective view of the gearbox mounting bracket showing the trough that captures any spilt waste reagent.
Figure 15:
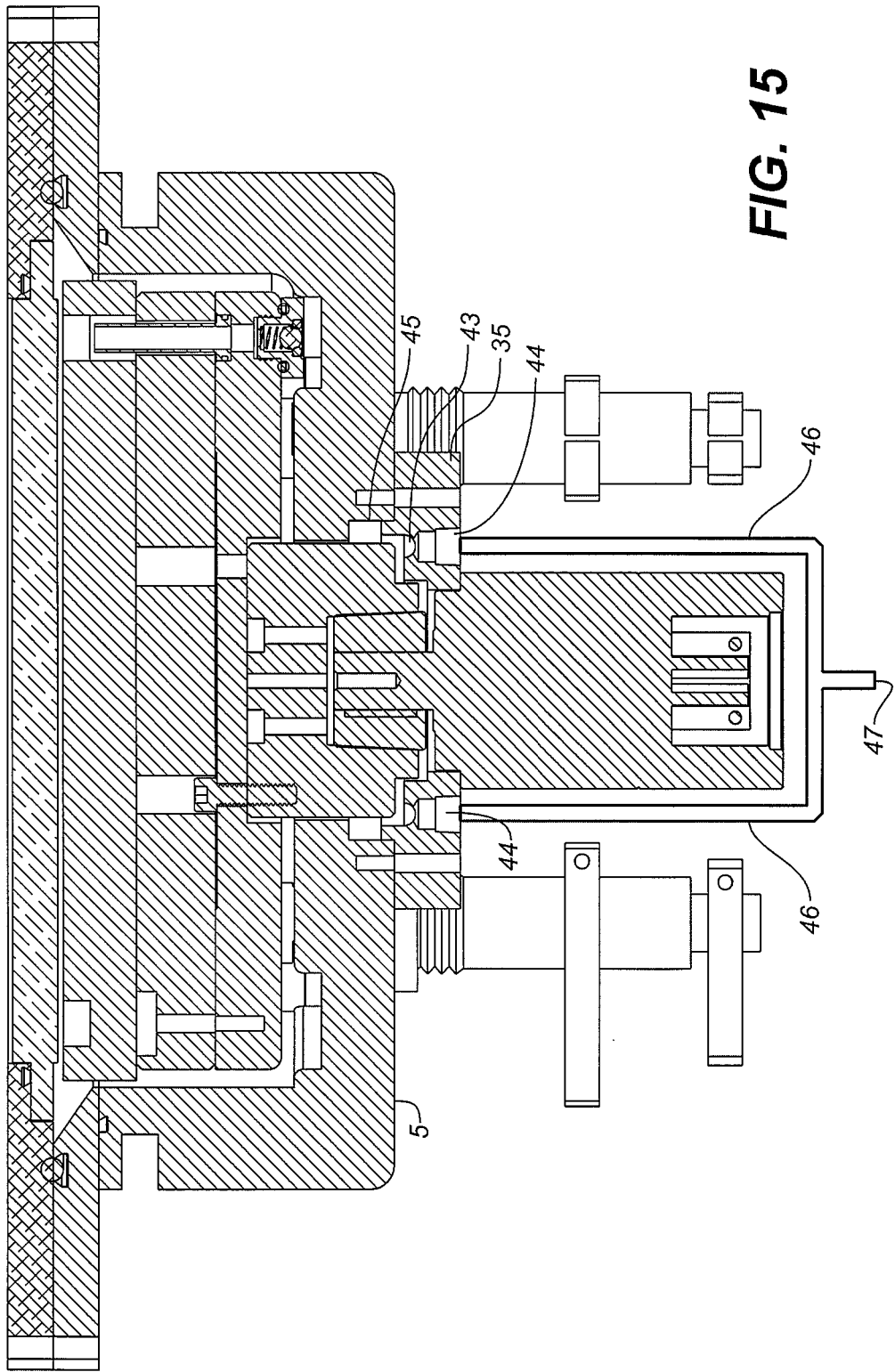
FIG. 15 is a cross section of the system showing the gearbox mounting bracket mounted in the system. The drain path for spilt waste reagent is identified in this figure.

With reference to FIGS. 14 and 15, the bowl 5 includes means to capture and divert waste that escapes to normal waste disposal system. This includes a gearbox/motor mount 35 that includes an annular trough 43 machined into the surface. Any spilled waste from the rotor will flow into annular trough 43. Four drain holes 44 are machined into motor mount 35. The drain holes 44 are connected to a waste container 47 through tubes 46 as shown in FIG. 15.

What is claimed is:

1. A solid phase synthesizer reaction system, of a type utilizing a plurality of flow through reaction vessels, each reaction vessel having an open top to allow introduction of reagents through said reaction vessel, an open bottom of each reaction vessel to allow liquid to flow from said reaction vessel and a solid phase reaction material within each of said reaction vessel between said open top end and open bottom end, said system comprising:

a rotor configured to hold a plurality of reaction vessels;
a cover positioned above said rotor;
an upper sealable chamber on said rotor, said reaction vessel open tops within said upper sealable chamber;
a lower sealable chamber within said rotor, said reaction vessel open bottoms within said lower sealable chamber;
a controllable pressure regulation pathway between said upper sealable chamber and said lower sealable chamber, said controllable pressure regulation pathway allowing equalization of pressure between said upper chamber and said lower chamber without requiring that gas pass through said reaction vessels.

2. The system of claim 1, wherein said lower sealable chamber includes a plurality of lower sealable chambers, each lower chamber including a plurality of reaction vessel open bottoms.

3. The system of claim 1, wherein said rotor includes a priming port.

4. The system of claim 1, further including a first drain system positioned on said rotor to drain liquid and gasses flowing through said reaction vessels into said lower sealable chamber and a second drain system connectable to said lower sealable chamber, said second drain system allowing draining gas only and allowing draining at a selectable flow rate.

5. The system of claim 1, further including a plurality of reagent dispense nozzles on said cover, and a motor mounted to said rotor to allow rotational positioning of said rotor such that a dispense nozzle can be selectively positioned above an open top of a reaction vessel.

6. The system of claim 1, further including a motor to turn said rotor and a motor mount onto which said motor is mounted, said motor mount having a spill channel to collect spilled waste and a drain to drain said spill channel.

7. The system of claim 4, wherein said second drain system in said lower sealed chamber includes a manifold, at least a first and a second calibration tube receiving gas flow from said manifold, and at least a first and a second valve regulating flow through respectively through said first and second calibration tube.

8. The system of claim 4, wherein said first drain system includes a ball check valve.

9. The system of claim 1, further including a central spacer on said rotor, said spacer located on a top, central position on said rotor just below said cover, said spacer limiting a gas volume in said upper sealable chamber.

10. A solid phase synthesizer reaction system, of a type utilizing a plurality of flow through reaction vessels, each reaction vessel having an open top to allow introduction of reagents through said reaction vessel, an open bottom of each reaction vessel to allow liquid to flow from said reaction vessel and a solid phase reaction material within each of said reaction vessel between said open top end and open bottom end, said system comprising:
a rotor configured to hold a plurality of reaction vessels;
a cover positioned above said rotor;
a sealable chamber within said rotor, said reaction vessel open bottoms within said sealable chamber;
a first drain connectable to said lower sealed chamber, configured to allow only gas flow from said lower sealable chamber and having a controllable flow rate regulation system;
a first drain control valve, configured to open or close flow through said first drain;
a second drain positioned within said lower sealable chamber such that it drains both gas and liquid from said chamber; and
a second drain control valve configured to open or close flow through said second drain.

11. The system of claim 10, wherein said first drain includes a drain pipe, a manifold joined to said drain pipe and a plurality of calibration tubes receiving flow from said manifold, each calibration tube having an associated valve that controls flow through each of said calibration tube.

12. The system of claim 10, wherein said second drain has a drain rate between 2 and 100 times greater than said first drain.

13. The system of claim 10, wherein said second drain control valve is a ball check valve.

14. The system of claim 10, wherein said first drain includes an initial outflow passageway from said sealable chamber that is out of line with a longitudinal axis of reaction vessels held on said rotor.

15. A method for control of flow through reaction vessels during solid phase synthesis reaction, wherein said reaction vessels each have an open top end, an open bottom, said reaction vessels positioned on a rotor such that said open bottom end is enclosed in a sealable chamber within said rotor, said method comprising:
equalizing a pressure utilizing a passageway that connects between an area holding said reaction vessel open top and said sealable chamber without flow through said reaction vessel, thereby limiting flow through said reaction vessel; and
Opening a variable flow rate gas drain to controllably drive fluid flow through said reaction vessels.

16. The method of claim 15, further including sealing said variable flow rate gas drain to seal said sealable chamber.

17. The method of claim 15, further including a further step of opening a second drain in said sealable chamber, said second drain providing flow draining of liquid and gas from said sealable chamber at a flow rate higher than a flow rate of said variable flow rate gas drain.

* * * * *